US008940867B2

(12) United States Patent
Miller et al.

(10) Patent No.: US 8,940,867 B2
(45) Date of Patent: Jan. 27, 2015

(54) PAN-ANTIVIRAL PEPTIDES

(75) Inventors: Kent D. Miller, Ormond Beach, FL (US); Billy S. Austin, Lake Mary, FL (US)

(73) Assignee: Nuovo Biologics, LLC, Miami, FL (US)

( * ) Notice: Subject to any disclaimer, the term of this patent is extended or adjusted under 35 U.S.C. 154(b) by 1375 days.

(21) Appl. No.: 11/778,871

(22) Filed: Jul. 17, 2007

(65) Prior Publication Data

US 2008/0161538 A1    Jul. 3, 2008

Related U.S. Application Data

(62) Division of application No. 11/648,773, filed on Dec. 29, 2006, now Pat. No. 7,259,237.

(51) Int. Cl.
*C07K 1/107* (2006.01)
*A61K 38/02* (2006.01)
*C07K 14/46* (2006.01)
*C07K 1/00* (2006.01)
*A61K 38/00* (2006.01)

(52) U.S. Cl.
CPC ............... *C07K 1/006* (2013.01); *C07K 14/46* (2013.01); *A61K 38/00* (2013.01)
USPC ............................. 530/345; 530/300; 514/3.7

(58) Field of Classification Search
CPC .......... A61K 38/00; A61K 45/06; A61K 8/64
See application file for complete search history.

(56) References Cited

U.S. PATENT DOCUMENTS

| | | | |
|---|---|---|---|
| 3,888,877 A | 6/1975 | Lehn | |
| 3,888,977 A | 6/1975 | Sanders | |
| 4,126,676 A | 11/1978 | Sanders | |
| 4,162,303 A | 7/1979 | Sanders | |
| 4,341,762 A | 7/1982 | Haast | |
| 4,741,902 A | 5/1988 | Haast | |
| 5,182,260 A | 1/1993 | Maraganore et al. | |
| 5,565,431 A | 10/1996 | Lipps et al. | |
| 5,676,974 A | 10/1997 | Valdes et al. | |
| 5,723,477 A | 3/1998 | McDonald et al. | |
| 5,859,187 A | 1/1999 | Matthews et al. | |
| 5,955,303 A | 9/1999 | Au-Young et al. | |
| 5,989,857 A | 11/1999 | Mundschenk | |
| 5,994,515 A | 11/1999 | Hoxie | |
| 6,613,745 B1 | 9/2003 | Gopalakrishnakone et al. | |
| 6,670,148 B2 | 12/2003 | Mundschenk et al. | |
| 7,259,237 B1 * | 8/2007 | Miller et al. | 530/345 |
| 7,348,400 B2 | 3/2008 | Livett et al. | |
| 7,807,635 B1 | 10/2010 | Miller et al. | |
| 7,902,152 B2 | 3/2011 | Reid et al. | |
| 8,034,777 B2 | 10/2011 | Reid et al. | |
| 2002/0150975 A1 | 10/2002 | Methfessel et al. | |
| 2003/0211465 A1 * | 11/2003 | Mundschenk et al. | 435/5 |
| 2004/0077545 A1 | 4/2004 | Lipps et al. | |
| 2004/0192594 A1 | 9/2004 | Reid et al. | |
| 2005/0031608 A1 | 2/2005 | Reid et al. | |
| 2005/0255097 A1 | 11/2005 | Reid et al. | |
| 2006/0088843 A1 | 4/2006 | Reid et al. | |
| 2006/0088858 A1 | 4/2006 | Reid et al. | |
| 2006/0229588 A1 | 10/2006 | Demopulos et al. | |
| 2008/0081048 A1 | 4/2008 | Raymond et al. | |
| 2008/0107752 A1 | 5/2008 | Reid et al. | |
| 2008/0161538 A1 | 7/2008 | Miller et al. | |
| 2008/0248992 A1 | 10/2008 | Mundschenk et al. | |
| 2008/0254137 A1 | 10/2008 | Raymond et al. | |
| 2009/0118503 A1 | 5/2009 | Sprott et al. | |
| 2009/0209468 A1 | 8/2009 | Reid et al. | |
| 2009/0304710 A1 | 12/2009 | Park et al. | |
| 2011/0183884 A1 * | 7/2011 | Miller et al. | 514/1.1 |
| 2011/0311642 A1 | 12/2011 | Reid | |

FOREIGN PATENT DOCUMENTS

| | | |
|---|---|---|
| CN | 1337404 | 2/2002 |
| WO | WO 99/24055 | 5/1999 |
| WO | WO 01/70173 | 9/2001 |
| WO | WO 2009/105585 | 8/2009 |

OTHER PUBLICATIONS

Tu, Anthony, Neurotoxins of Animal Venoms: Snakes. Department of CHemistry, COlorado State University, p. 235-258, 1973.*
Nicastro et. al. Solution Structure of crotamine, a Na+ channel affecting toxin from *Crotalus durrisus* trafficus venom; Eur. J. Biochem. (270) 1969-1979, 2003.*
He et. al. Cloning and Purification of α-neurotoxins from king cobra (*Ophiophagus hannah*) Toxicon (44), 295-303, 2004.*
Shiu et. al. Solution Structure of γ- Bungarotoxin: The Functional Significance of Amino Acid Residues Flanking the RGD Motif in Integrin Binding, Proteins: Structure, Function, and Bioinformatics, 57: 839-849, 2004.*
Hudson et. al. Experimental allergic encephalomyelitis: Prevention with a nontoxic derivative of a cobra neurotoxin, Mol. Immunol. 20(2) 1983.*
Yang et. al. Optical Rotary Dispersion of Cobratoxin, The Journal of Biochemistry, vol. 61, No. 2, 1967.*
Austin et al., "FELV and FIV Cats Sera-Convert to Negative with Panavira," Journal of the American Holistic Veterinary Medical Association, vol. 28(1), pp. 28-29.

(Continued)

*Primary Examiner* — Thomas S. Heard
*Assistant Examiner* — Jeanette Lieb
(74) *Attorney, Agent, or Firm* — Sheridan Ross P.C.

(57) ABSTRACT

Methods for preparing viral neuraminidase inhibitors including antiviral peptides by specifically chemically modifying disulfide bonds in precursor molecules. A method of inhibiting viral neuraminidases by administering a viral neuraminidase inhibitor comprising an antiviral peptide prepared by the above methods and inhibiting the viral neuraminidase. Therapeutics for inhibiting viral neuraminidases, including effective amounts of viral neuraminidase inhibitors including antiviral peptides derived from selectively chemically modified disulfide bonds in precursor molecules, and present in a pharmaceutically acceptable carriers.

24 Claims, 10 Drawing Sheets

(56) References Cited

OTHER PUBLICATIONS

Bodian et al., "The rate of progression of poliomyelitis virus in nerves," Bulletin of the Johns Hopkins Hospital, 1941, vol. 69, pp. 79-85.
Bracci et al., "Molecular Mimicry Between the Rabies Virus Glycoprotein and Human Immunodeficiency Virus-1 GP120: Cross-Reacting Antibodies Induced by Rabies Vaccination," Blood, 1997, vol. 90(9), pp. 3623-3628.
Burmeister Getz et al., "A Comparison between the Sulfhydryl Reductants Tris(2-carboxyethyl)phosphine and Dithiothreitol for Use in Protein Biochemistry," Anal. Biochem., 1999, vol. 273, pp. 73-80.
Chang et al., "Disulfide isomerization and thiol-disulfide exchange of long neurotoxins from the venom of *Ophiophagus hannah*," Arch Biochem Biophys, online publication Aug. 2006, vol. 454(2), pp. 181-188.
Chen et al., "A long-form alpha-neurotoxin from cobra venom produces potent opioid-independent analgesia," Acta Pharm. Sin., 2006, vol. 27(4), pp. 402-408.
Crawford et al., "Transmission of Equine Influenza Virus to Dogs," Science, 2005, vol. 310, pp. 482-485.
Crestfield et al., "The Preparation and Enzymatic Hydrolysis of Reduced and S-Carboxymethylated Proteins," The Journal of Biological Chemistry, 1963, vol. 238(2), pp. 622-627.
DuPont Oxone® Monopersulfate Compound Technical Information, date unknown, 6 pages.
Fabricant et al., "Nerve growth factor receptors on human melanoma cells in culture," Acad Sci USA, 1977, vol. 74, pp. 565-569.
Gordon et al., "Phosphorylation of acetylcholine receptor by endogenous membrane protein kinase in receptor-enriched membranes of *Torpedo californica*," Nature, 1977, vol. 267, pp. 539-540.
Gordon et al., "Phosphorylation of Membrane Proteins at a Cholinergic Synapse," Proc. Natl. Acad. Sci., 1977, vol. 263-267.
Huang et al., "A rapid and sensitive assay method for protein kinase," Anal. Biochem., 1976, vol. 72, pp. 593-599.
Iida et al., "Protein kinase activity is associated with CD63 in melanoma cells," J Transl Med, 2005, vol. 3, pp. 42-50.
Johansson et al., "Variation in the Divalent Cation requirements of Influenza A Virus N2 Neuraminidases," J. Biochem., 2003, vol. 134, pp. 345-352.
Kasherov et al., "Benzophenone-type photoactivatable derivatives of alpha-neurotoxins and alpha-conotoxins in studies on Torpedo nicotinic acetylcholine receptor," J. Recept. Signal Trans. Res., 1999, vol. 19(1-4), pp. 559-571.
Kuo et al., "Cobra polypeptide cytotoxin I and marine worm polypeptide cytotoxin A-IV are potent and selective inhibitors of phospholipid-sensitive Ca2+-dependent protein kinase," FEBS Letters, Mar. 1983, vol. 153(1), pp. 183-186.
Lamb et al., "On the action of venoms of different species of poisonous snakes on the nervous system," Lancet, 1904, vol. 1, pp. 20-22.
Lentz et al., "Amino acid sequence similarity between rabies virus glycoprotein and snake venom curaremimetic neurotoxins," Science, 1984, vol. 226, pp. 847-848.
Lentz, Thomas L., "Structure-Function Relationships of Curaremimetic Neurotoxin Loop 2 and of a Structurally Similar Segment of Rabies Virus Glycoprotein in Their Interaction with the Nicotinic Acetylcholine Receptor," Biochem., 1991, vol. 30, pp. 10949-10957.
Matsuda et al., "In vitro demonstration of neural transmission of avian influenza A virus," J. of General Vir., 2005, vol. 86, pp. 1131-1139.
Miller et al., "Inhibition of Virus-Induced Plaque Formation by Atoxic Derivatives of Purified Cobra Neurotoxins," Biochimica et Biophysica Acta., 1977, vol. 496, pp. 192-196.
Mori et al., "Selective targeting of habenular, thalamic midline and monoaminergic brainstem neurons by neurotropic influenza A virus in mice," Journal of Neurovirology, 1999, vol. 5, pp. 355-362.
Mundy et al., "A randomized controlled study of modified cobratoxin in adrenomyeloneuropathy," Neurology, 2003, vol. 61, pp. 528-530.
Nambiar et al., "Signaling Networks in Cutaneous Melanoma Metastasis Identified by Complementary DNA Microarrays," Arch Dermatol, 2005, vol. 141, pp. 165-173.
Neri et al., "Sequence homology between HIV gp120, rabies virus glycoprotein, and snake venom neurotoxins is the nicotinic acetylcholine receptor an HIV receptor?" Arch Virol., 1990, vol. 114, pp. 265-269.
Ruegg et al., "Reductive Cleavage of Cystine Disulfides with Tributylphosphine," Methods in Enzymol, 1977, vol. 47, pp. 111-116.
Saitoh et al., "Change in state of phosphorylation of acetylcholine receptor during maturation of the electromotor synase in *Torpedo marmorata* electric organ," Proc. Natl. Acad. Sci., 1981, vol. 78, pp. 4430-4434.
Sanders et al., "Neurotoxoid Interference with Two Human Strains of Poliomyelitis in Rhesus Monkeys," New York Academy of Sciences, 1953, vol. 58, Art. 1, pp. 1-12.
Sela et al., "Reductive Cleavage of Disulfide Bridges in Ribonuclease," Science, 1957, vol. 125, p. 691-692.
Seller et al., "Protein kinase C isoforms in normal and transformed cells of the melanocytic lineage. Melanoma Research," 2002, vol. 12, pp. 201-209.
Teichberg et al., In vitro phosphorylation of the acetylcholine receptor, Nature, 1977, vol. 267, pp. 540-542.
The Bureau of Biologics, The National Institute of Neurological and Communicative Disorders and Stroke, and Johns Hopkins University: Workshop on Modified Neurotoxin Treatment of Amyotrophic Lateral Sclerosis, 1979, pp. 63-79.
Utkin et al., "[alpha-Neurotoxins and alpha-conotoxins—nicotinic cholinoreceptor blockers]," Bioorg. Khim., 1999, vol. 25(11), pp. 805-810 (article in Russian).
van Heyningen et al., "The fixation of tetanus toxin by ganglioside," J. Gen. Microbiol., 1961, vol. 24, pp. 107-119.
Walkinshaw et al., "Three-dimensional structure of the "long" neurotoxin from cobra venom," Proc. Natl. Acad. Sci. USA, 1980, vol. 77(5), pp. 2400-2404.
Wright et al., "The movements of toxin in the nervous system in experimental tetanus in rabbits," Brit. J. Exp. Path., 1951, vol. 32, pp. 169-182.
Yoon et al., "Influenza virus infection in racing greyhounds," Emerg Infect Dis, 2005, vol. 11, pp. 1974-1976.
Yourist et al., "Inhibition of Protein Kinases by Antiviral Cobra alpha-Neurotoxoid," Federation Proceedings, 1981, vol. 40, p. 300, Abstract 376.
Yourist et al., "Inhibition of Herpes Simplex Virus Replication by Cobra .alpha.-Neurotoxoid," J. Gen. Virol., 1983, vol. 64, pp. 1475-1481.
International Search Report and Written Opinion for International (PCT) Patent Application No. PCT/US11/22200, mailed Mar. 30, 2011.
Billy S. Austin, DVM; Kent D. Miller, PHD, MD; FELV and FIV Cats Sero-Convert to Negative with Panavira; Journal of the American Holistic Veterinary Medical Association; pp. 28-29; vol. 28, No. 1, 2009.
International Preliminary Report on Patentability for International (PCT) Patent Application No. PCT/US11/22200, mailed Aug. 2, 2012, 7 pages.
Database WPI, Thomson Scientific, London, GB; AN 2002-384228, XP007217147, & CN 1337404A, Feb. 27, 2002 *abstract*.
Extended Search Report for European Patent Application No. 11735292.2, dated Dec. 6, 2013 7 pages.

* cited by examiner

Figure 9. Inhibition of Influenza A Neuraminidase by Alpha-Neurotoxin. Plot of Neuraminidase Inhibition (-pmol/Min) versus pmol Toxin.

US 8,940,867 B2

PAN-ANTIVIRAL PEPTIDES

CROSS-RELATED REFERENCE SECTION

This application is a divisional application of U.S. patent application Ser. No. 11/648,773, filed Dec. 29, 2006, now U.S. Pat. No. 7,259,237, which is incorporated herein by reference.

BACKGROUND OF THE INVENTION (1) Field of the Invention

The present invention relates to novel antiviral peptides and preparations. More particularly, the invention relates to antiviral peptides derived from venom alpha-neurotoxins, and are capable of inhibiting viral neuraminidases.

(2) Description of Related Art

There are several sources of toxins that can be harmful to both humans and animals, such as radiation, inorganic and organic substances. Neurotoxins are toxins which specifically affect neurons through interaction with membranes and ion channels. Most animal venoms can be classified as neurotoxins, such as those found in bees, snakes, scorpions, and spiders. Detoxification of such neurotoxins is a goal when treating those affected. Also, antiviral solutions can be derived from neurotoxins.

Sanders, M., et al., (Ann. N.Y. Acad. Sci. (1953) 58: 1-12) discloses multiple species of snake venoms detoxified by chemical oxidation. An antiviral test system measured effects of the venom derivatives on survival rates of rats, mice, and monkeys experimentally infected with polio viruses. The choice of chemical reactions was of prime importance. Oxidative detoxification of one class of whole venoms produced antiviral activities. Detoxifications by reaction with formaldehyde produced inert materials. The significance of the differences in reactivity was two-fold. First, the formaldehyde-treated group served as an excellent control for the active, oxidized venoms because the test animals in the two groups received the same quantities of venom, thus negating nonspecific protein interactions as the cause of the difference in activity. Second, if the active ingredients in the venoms were proteins, a fact not known at the time, the chemical groups modified by the formaldehyde could be implicated in the antiviral effect. Of prime importance was restriction of the antiviral activities to oxidatively detoxified venoms that contained alpha-neurotoxins. Those venoms included all species of cobras tested, and the Banded Krait and South American rattlesnake, Crotalus duressus terrificus.

Twenty two years later one of the present inventors proved, through separations technology, that the specific precursors of the antiviral activities in neurotoxic venoms were the alpha-neurotoxins (Miller, et al., Biochim. Biophys. Acta (1975) 496: 192-196). The alpha-neurotoxins from two of the venoms, the Thailand cobra and the Banded Krait, were isolated in chemically pure form and detoxified by the identical oxidation reaction employed in the original work by Sanders. Antiviral activities of those materials were quantitated by reductions of plaque counts formed by the Semliki Forest Virus (a neurotropic virus like the polio virus) on cultured sheets of baby hamster kidney (BHK) cells. Detoxification by reduction and alkylation of the toxins produced the same nontoxic antiviral peptide actions. (Miller, K. D., in "Workshop on Modified Neurotoxin: Treatment of Amyotrophic Lateral Sclerosis", Bureau of Biologicals, NINCDS, Apr. 5, 1979: p 63-76). Investigations continued with evaluations of those purified antiviral polypeptides in several tissue culture and animal test systems employing the herpes simplex virus (Yourist, J. E., et al., J. Gen. Virol. (1983) 64: 1475-1481). Further, Yourist demonstrated inhibition of several protein kinases, including a protein kinase derived from human myelin, by both the oxidized and reduced and alkylated peptides (Yourist, J E, Doctoral dissertation, University of Miami, 1979).

Important to an understanding of the present invention are the similarities in chemical structures among a wide variety of animal alpha-neurotoxins. Those similarities include closely related amino acid sequences in key parts of the toxin molecules (Yang, C. C., Toxicon, (1974) 12: 143). A rigid tertiary conformation of the conserved region after detoxification by disulfide bond scission is suggested by the triple-stranded beta-pleated sheet structure of the native toxin as reported by Walkinshaw (Proc. Nat. Acad. Sci. (1980) 77: 2400-2404).

Antiviral peptides derived from alpha-neurotoxins are formed by scission of the toxin disulfide bonds with resultant conformational changes and elimination of toxicity. Use of strong oxidants for this purpose is problematic because this may result in modifications of other amino acids in these peptides, especially tyrosine, histidine, tryptophane and lysine, common constituents of the alpha-neurotoxins (Yang, C. C., Toxicon (1974) 12: 1-43; Elliott, K. A. C., Ann. Rev. Biochemistry, (1946) 15, 1-34; Thompson, E. O. P., Biochim. Biophys. Acta, (1954) 15, 440; Stahman, M. A. and Spencer, A. K., Biopolymers, (1977) 16, 1299-1306). Such inadvertent reactions induce heterogeneity into the final reaction products.

Therefore, it would be desirable to use selective disulfide bond oxidants to generate antiviral peptides. As detailed below, the oxidant, potassium monopersulfate (E.I. Dupont de Nemours & Co., Wilmington, Del.), employed herein, is an alternate reagent that specifically oxidizes the sulfur-containing amino acids, cystine and cysteine, without the undesirable alterations cited above.

An alternate means for specific scission of disulfide bonds is through specific reductions, with subsequent alkylations of the resultant sulfhydryl groups with adducts that prevent reoxidation. Such reactions are commonly employed in determination of protein structure (Sela, M., White, F. H., and Anfinsen, C. B., Science, (1957) 691-692; Crestfield, A. M., Moore, S., and Stein, W. H., J. Biol. Chem., (1963) 238, 622). While reductions with sulfhydryl compounds such as dithiothreital and beta-mercaptoethanol are commonly employed, the phosphenes used herein represent alternative reductants for the same purpose of reducing the disulfide bonds in proteins (Ruegg, U. T. and Rudinger, J., Methods in Enzymol., (1977) 47, 111-126; Getz, E. B., Xiao, M., Chakrabarty, T., et al, Anal. Biochem. (1999) 273, 73-80).

The present invention also utilizes reduction reactions for generation of antiviral peptides that are viral neuraminidase inhibitors, procedures that likewise avoid inadvertent modifications of chemical groups required for full therapeutic effects. In addition, an important objective of the present invention is to obtain a subset of antiviral peptides utilizing reduction and alkylation based on selection, from a list of alkylating agents, of adducts that block the reoxidation of the disulfide bonds when the excess reductants are removed from the peptides. As detailed below, selections among those adducts can yield compounds that, through introduction of highly sensitive markers, permit (1) detailed studies of the interactions between the respective peptide and the virus preparations, and (2) modulation of interactions with the viral neuraminidases.

As detailed below, the antiviral peptides of the invention are useful for inhibiting viral neuraminidases and thus inhibiting viral infections. The myxoviruses are comprised of two families, the orthomyxoviruses and paramyxoviruses. Orthomyxoviruses include the Influenza viruses A, B, and C. Influenza A is associated with the most severe form of human influenza. It can infect a variety of mammals and birds. Birds and pigs can serve as reservoirs from which the virus can jump to humans, dogs, and other animals. One particularly prevalent subtype of Influenza A is the "avian flu", subtypes generally denoted by HxNy. The "avian flu" is highly contagious and dangerous, especially with mutations that cannot be vaccinated against before such mutations have occurred. Paramyxoviruses 1 and 3 likewise cause flu-like symptoms but less severe than those of the Influenza A virus. Among other paramyxoviruses are the mumps virus, the Sendai virus (a mouse pathogen), and the Newcastle Disease virus, an important avian virus. On the surfaces of those viruses are two glycoproteins that contribute to viral infectivity and replication processes. One, a hemagglutinin, serves as the receptor-binding function for viral attachment to permissive cells. The other glycoprotein, a neuraminidase, facilitates release of newly formed virus particles that assemble in clusters inside the infected cells. The release is attributed to the hydrolytic cleavage of sialic acid residues by that enzyme. Thus, neuraminidase inhibitors are modulators of virus dissemination.

A clinical need for agents that block myxovirus production (e.g., influenza A virus) arises when the viruses undergo antigenic drift such that antibodies to a contemporary vaccine are rendered ineffective. Effective therapeutic compounds, zanamivir and oseltamivir, function well when administered early in the infectious process. Both compounds are analogues of sialic acid and function as inhibitors of the viral neuraminidase, thus inhibiting release of newly-generated varions from the infected cells, and blocking spread of the disease.

Historic evidence of a neurotropic component to the influenza A virus of the 1918 pandemic was suggested by reports of major CNS disturbances (Crookshank, F. G., Lancet, (1919) 1, 79-80). Neurotropic strains of influenza A virus were found to infect the brain stem via the olfactory bulb (Mori, I., Diehl, A. D., Chauhan, A., et al., J. Neurovirol. (1999) 5, 355-362), and axonal transport of the virus was clearly demonstrated (Matsuda, K., Shibata, T., Sakoda, Y., et al., J. Gen. Virol. (2005) 86, 1131-1139). The peptides described herein contain amino acid sequences common to components of surface proteins of some neurotropic viruses such as rabies viruses (Lentz, T. L., Hawrot, E., and Speicher, D. W., Science (1984) 226, 847-848: Lentz, T. L. Biochemistry, (1991) 30, 10949-57). Likewise, a glycoprotein constituent of the HIV virus displays an amino acid sequence homology with that of the rabies viruses and alpha-neurotoxins (Neri, P., Bracci, L., Rustici, M., et al., Arch. Virol. (1990) 114, 265-269: Bracci, L., Ballas, S. K., et al., Blood, (1997) 90, 3623-3628). The contribution of those structures to inhibition of myxovirus neuraminidases is suggested by peptide-virus complexes described herein.

In addition to treatment of human patients with myxovirus infections, an additional target for this invention is application of the products to treatments of a broad range of veterinary diseases. Recent evidence suggests that the influenza viruses can jump to dogs and other animals that may serve as viral reservoirs. Acute and chronic respiratory and/or gastrointestinal viruses are a constant problem in veterinary practice. Contagion expresses itself where dogs and cats are confined in animal hospitals, boarding facilities, pet stores, animal control facilities, zoos, etc. Viral infections affecting dogs include canine distemper, adenovirus type 2, corona virus, and the parainfluenza and parvoviruses. Among other infectious diseases affecting cats are rhinotracheitis, calici virus, panleukopenia and herpes viruses. Mortality rates in these infections are relatively high, especially in young animals. The diseases are spread by close contact with other animals or by contact with body discharges as result from coughing, sneezing, fecal contamination, etc. Other diseases are spread by more intimate contact such as by copulation, fighting, birthing, etc. Diseases acquired by those modes include feline leukemia (FeL) and infection with the feline immunodeficiency virus (FIV). Therefore, there is a need for antiviral peptides capable of treating or vaccinating against diseases affecting both humans and animals.

BRIEF SUMMARY OF THE INVENTION

The present invention provides methods for preparing viral neuraminidase inhibitors including antiviral peptides, including chemical steps that specifically modify disulfide bonds in precursors of those neuraminidase inhibitors.

The present invention also provides for a method of inhibiting viral neuraminidases, including the steps of administering a viral neuraminidase inhibitor including an antiviral peptide prepared by the above method, and inhibiting the viral neuraminidase.

The present invention further provides pharmaceutically acceptable therapeutic viral neuraminidase inhibitors as derived by the selective chemical modifications of disulfide bonds in neurotoxin precursors.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein:

Figure 1:
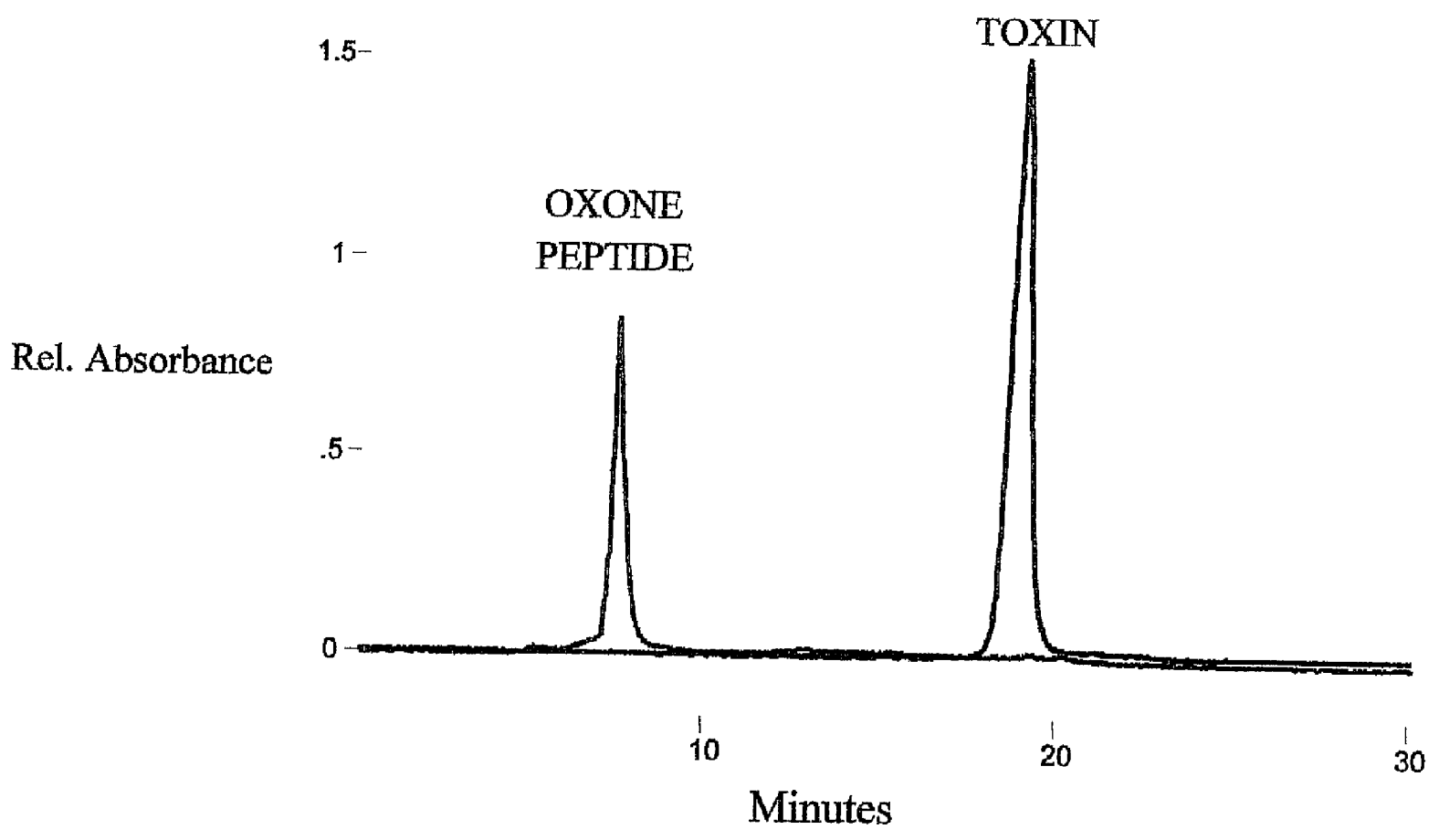

FIG. 1 is a graph displaying the chromatographic character of a potassium monopersulfate-oxidized antiviral peptide compared to that of the neurotoxin from which it was derived. A TOSOH TSK-GEL G3000PW column is equilibrated with purified water. After injection of each peptide a linear, aqueous gradient of tetrabutylammonium hydrogen sulfate is applied for 30 minutes to a final concentration of 5 mM.

FIG. 3 is a graph that documents the inhibition of the neuraminidase of the canine parainfluenza virus by (1) the purified cobra alpha-neurotoxin, (2) its potassium monopersulfate-oxidized derivative, and (3) its reduced, alkylated derivative, alkylation in this case with iodoacetamide. The substrate is MUN. Incubations are at 37° C., in 0.10 M chloride-free acetate buffer, pH 5.5, for 60 minutes.

FIG. 6 is a graph displaying that the neuraminidase inhibitory activity of the alpha-neurotoxin and its nontoxic derivatives appear specific for the viral enzyme, not for the respective enzymes derived from bacteria or mammals. In this case the source of the mammalian neuraminidase is a pool of dilute sputa from patients with pulmonary tuberculosis. The bacterial neuraminidase is of *Vibrio cholerae* origin. The inhibitory peptide in this case is the unmodified, active alpha-neurotoxin.

FIG. 9 is a graph displaying that Influenza A neuraminidase is also inhibited by the peptides, in this case by the parent neurotoxin, with calcium ions required for the phenomenon.

DETAILED DESCRIPTION OF THE INVENTION

Figure 2:
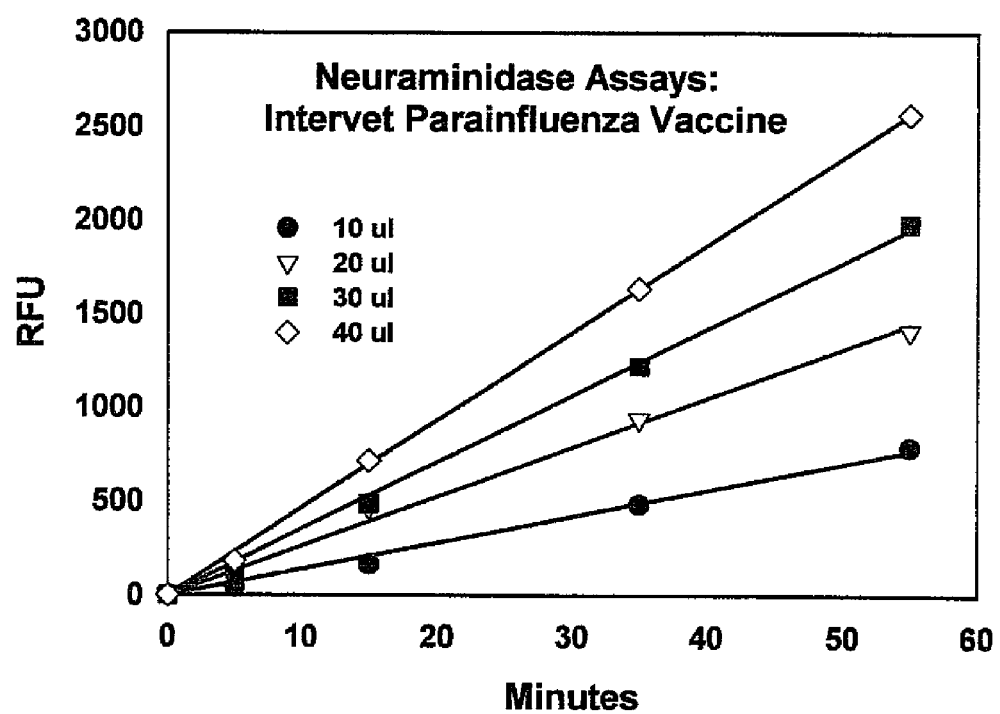
FIG. 2 is a graph displaying the linear rates of hydrolysis of the neuraminidase substrate, 2-(4-methylumbelliferyl)-a-D-N-Neuraminic acid (MUN), by varying amounts of a live, attenuated canine parainfluenza vaccine (Intervet, Inc.). Inhibition of this and other myxovirus neuraminidases, documented herein, provides one means for quantitative measurement of potencies of the antiviral peptides. Reactions are in 0.10 M chloride-free acetate buffer, pH 5.5. The stop buffer for the reactions is 0.2 M glycine buffer, pH 10.4, 25 percent with respect to ethanol.

The present invention provides methods and therapeutic viral neuraminidase inhibitors that are antiviral peptides. The present invention further provides methods of producing such viral neuraminidase inhibitors of antiviral peptides for inhibiting viral neuraminidases by selectively chemically modifying disulfide bonds of the antiviral peptides.

"Antiviral peptides" are defined herein to include peptides derived from alpha-neurotoxin precursor molecules. These peptides possess viral inhibitory activity including the ability to inhibit viral neuraminidases, such as the neuraminidases of myxoviruses and paramyxoviruses. The peptides are formed by the elimination of disulfide bonds, which changes the conformation of the precursor toxins and eliminates previous toxicity. The antiviral peptides herein are not restricted to amino acid chain lengths. Alpha-neurotoxins have two different structural forms—Type I (approximately 60 amino acids with four disulfide bonds) and Type II (approximately 73 amino acids with 5 disulfide bonds). Antiviral peptides can also be derived from various viruses and bacteria. For example, antiviral peptides have been derived from herpes simplex virus 1, *Enterococcus mundtii* ST4V, C-terminal gamma interferon (IFN-gamma), T20, coronavirus, and *Amaranthus* tricolor leaves. It is contemplated that the present invention would be applicable to other viruses and bacteria precursor molecules that share structure with alpha-neurotoxins (i.e. common amino acid sequences).

"Neuraminidases" are defined herein as an antigenic glycoprotein enzyme found on the surface of a virus in a protruding shape. There are several different subtypes. The function of neuraminidase is to aid in the release of viruses from cells and to prevent viruses from aggregating. Inhibition of neuraminidases is a goal in preventing the spread of a virus.

The present invention arose from, and intensified with, the discovery of the antiviral effects of the peptides on the Sendai Virus (SV), a paramyxovirus and mouse pathogen. Rapid advances toward understanding one mechanism of antiviral action of the peptides were then possible with the further discovery that both the alpha-neurotoxins and, most importantly, their respective nontoxic derivatives, inhibit the neuraminidases of a variety of myxoviruses.

A quantitative assay system for measurement of viral neuraminidases permitted an increasingly detailed understanding of the peptide-induced enzyme inhibition reaction. Stable quality control enzyme preparations, prepared from sputa of patients with pulmonary tuberculosis, assure the accuracy and precision of the analytic system.

Neuraminidase inhibition by the alpha-neurotoxins and their nontoxic derivatives appears specific for the viral enzymes, more so than for bacterial and mammalian neuraminidases.

Two types of preparations of viral neuraminidase inhibitors including antiviral peptides described herein assure minimal heterogeneity of the products. The reduced, alkylated subset of the new peptides is particularly useful to an understanding of the mechanisms of the antiviral phenomenon. Substitutions with selected alkylating agents permit introduction of stable, sensitive markers into the molecules without affecting the mechanism of action. For example, a fluorescent marker was introduced into a nontoxic reduced, alkylated alpha-neurotoxin derivative that retained its ability to inhibit the viral neuraminidase. In some such cases, enzyme inhibition is enhanced by selected alkylations.

The salvage of chick embryos from infections with a myxovirus, cited above, prompted successful applications of the peptides as therapeutic agents for treatment of canine influenza and other diseases of veterinary practice recounted in this document.

The mechanism of neuraminidase inhibition by these polypeptides is markedly distinct from that of effective, small neuraminidase inhibitors such as the sialic acid analogues, Zanamivir and Oseltamivar. One distinction is the apparent high specificity of the peptides for the viral neuraminidases, a property not as obvious among the sialic acid analogues. Another distinction is the marked difference in compositions. The neuraminidase inhibitors of the present invention are polypeptides of relatively high molecular weight compared to those of the sialic acid analogues. Therefore, for therapeutic objectives one must expect markedly different pharmacokinetic properties between the two types of compounds.

Two methods for preparation of these antiviral peptides that inhibit viral neuraminidases involve minimal chemical changes to the parent alpha-neurotoxin molecules, resulting in improved purity. Those methods circumvent problems of prior oxidative procedures; namely, undesirable amino acid modifications and attendant microheterogeneity. Chemical purity of the new antiviral peptides is based on specific scissions of the disulfide bonds within the parent alpha-neurotoxins, with no modifications of other amino acids in those molecules. In other words, the disulfide bonds are selectively chemically modified.

The loss of secondary structure is known to cause alpha-neurotoxins to lose toxicity, as alpha-neurotoxins are dependent on intact disulfide bonds. One of the two forms of the antiviral peptide claimed herein results from specific oxidation of the disulfide bonds employing the oxidizing agent, potassium monopersulfate. Potassium monopersulfate characteristically attacks sulfur atoms such as in disulfide and sulfhydryl groups. It has little effect on other amino acids such as tyrosine, tryptophane, and histidine, the latter group of amino acids also susceptible to modification by less specific oxidizing agents.

An example of preparation of a potassium monopersulfate-oxidized antiviral peptide is as follows. A known weight of the purified alpha-neurotoxin is mixed with 7-16 times its weight of dry potassium monopersulfate powder previously dissolved in purified water to a concentration of 12.8 percent. The mixture is stirred one hour at ambient temperature. Those conditions are adequate for the quantitative detoxification of a toxin molecule containing five disulfide bonds per molecule. The oxidized peptide is then freed of excess potassium monopersulfate by one of several methods. Those methods include the following:

a. Diafiltration employing semi-permeable membranes (i.e., Amicon UM-2 membranes) capable of retaining the peptide with elimination of the filterable low molecular weight products including potassium monopersulfate.

b. Chromatographic procedures on columns containing a gel permeation matrix (i.e., P-4 gel: Calbiochem Corp) capable of exclusion of the peptide and retardation of the low molecular weight residual potassium monopersulfate.

c. A convenient method for separation of the peptide from the potassium monopersulfate involves, first, dilution of the reaction mixture 10-fold with purified water. That dilute solution is applied to a column of octadecyl (C18) silica gel previously equilibrated with purified water. After washing with purified water for removal of the excess potassium monopersulfate, the peptide is eluted from the column with 35 percent reagent grade isopropanol. The eluate is collected in screw-capped glass bottles and extracted four times with n-octanol for removal of the isopropanol. The aqueous phase, which includes the peptide in water, is then extracted four times with pentane for removal of residual octanol. The last two pentane extraction mixtures are placed in the freezer. The pentane is decanted from the frozen, aqueous peptide preparation in each case, Finally, the last traces of pentane are driven off by holding the aqueous peptide solution, uncapped but with porous protection from contamination, at 50 degrees C. Demonstrations of the purity of potassium monopersulfate peptide preparations, and of the alpha-neurotoxin from which they are prepared, are demonstrated by the high performance liquid chromatographic pattern illustrated in FIG. 1.

Figure 5:
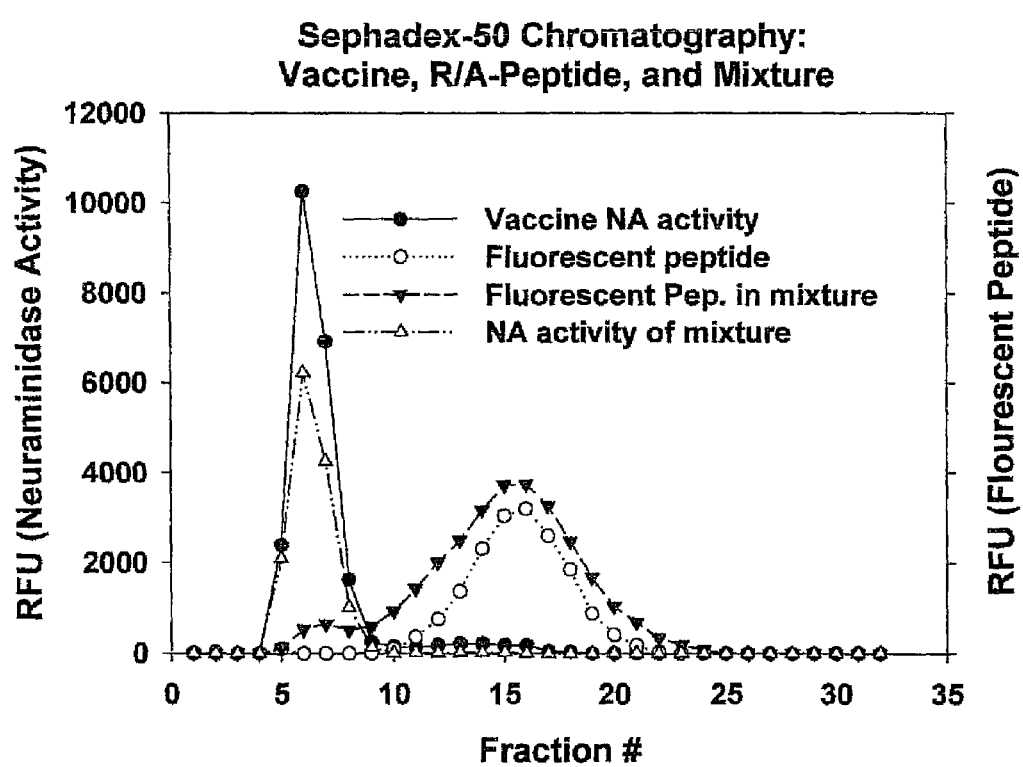
FIG. 5 is a graph displaying the chromatographic characteristics of (1) the neuraminidase activity of the live, canine parainfluenza vaccine, (2) a fluorogenic, reduced, alkylated antiviral peptide (IAEDANS-peptide), and, (3) significantly, the reduction of the neuraminidase activity peak in mixtures of the two reactants at pH 5.5. The chromatographic medium is Sephadex G-50. The solvent is 0.10 M chloride-free acetate buffer, pH 5.5. Fluorescence that reflects the neuraminidase activity of the virus alone and the residual activity in the virus-peptide mixture, are read from the left-hand ordinate. Fluorescence of the IAEDANS-peptide alone, and in the mixture, is read from the right-hand ordinate.

The second new group of viral neuraminidase inhibitors is created by the specific reduction of the disulfide bonds in the precursor neurotoxins. That chemical reaction requires addition of any of a group of blocking reactants that form covalent bonds with the reduced sulfhydryl groups. Such blocking agents (alkylating agents) prevent reoxidation and potential regeneration of toxic activity. Since a number of alkylating agents are available a subset of antiviral peptides are formulated, each a different alkylated derivative of the reduced neurotoxin. Examples of effective alkylating agents are iodoacetamide and iodoacetic acid. Other blocking agents, of major importance to an understanding of the peptide-viral enzyme interactions, insert highly sensitive markers into the basic reduced, alkylated peptide. An example is 5-((((iodoacetyl)amino)ethyl)amino)naphthalene-1-sulfonic acid (IAEDANS). The resultant fluorescent derivative not only retains its ability to inhibit the viral neuraminidases, but also reveals the related formation of complexes between the peptide and a constituent(s) of the respective virus preparation. Evidence further establishes that adducts provided by specific alkylating agents can increase the potency of the antiviral peptides (FIG. 5).

An example of preparation of one of the set of reduced, alkylated antiviral neuraminidase inhibitors is as follows. In this case the purified neurotoxin is dissolved in 6.0 M urea containing 0.01 M ethylenediamine tetraacetic acid buffer, pH 8.0. The solution is degassed with argon, followed by addition of dithiothreital. The mixture is stirred in the dark for 30 minutes for reduction of the disulfide bonds. A blocking compound, one of a variety of choices, is added to alkylate the resultant suifhydryl groups with the pH maintained at 7.0 with dilute ammonium hydroxide.

An alternate method for preparation of reduced, alkylated antiviral neuraminidase inhibitors involves use of the reducing agent, Tris-(2-carboxyethyl) phosphene. In a dark glass container, a quantity of purified toxin is weighed out and dissolved in 0.1 M HEPES buffer, pH 7.0. The mixture is degassed, purging with nitrogen or argon gas. A weight of Tris-(2-carboxyethyl) phosphene equal to five times the weight of toxin in the solution is added to the mixture. The mixture is stirred in a dark glass vessel for 30 minutes at ambient temperature. The mixture is chilled to 4-6° C., and, with stirring, an amount of dry iodoacetamide, iodoacetic acid, or other alkylation (blocking) agent of choice is added in an amount two to four times the molar quantity of the Tris-(2-carboxyethyl) phosphene in the mixture. After one hour, the mixture is diluted five-fold with purified water. The reduced alkylated mixture is loaded on an octadecyl silica gel column (C18) previously equilibrated with purified water.

After a thorough wash with purified water, the peptide is eluted from the column with 35 percent isopropanol. The aqueous peptide solution is cleared of isopropanol by four extractions with n-octanol followed by four extractions with pentane. The last two pentane extraction mixtures are frozen such that the pentane can be decanted from the frozen, aqueous peptide. The solution is then held at 50 degrees C. to drive off the residual pentane.

Purity of the nontoxic, antiviral peptide preparations described herein is evaluated by an all-aqueous high performance liquid chromatographic system (HPLC) that clearly distinguishes it from its neurotoxic precursor. An HPLC column, such as a 7.5×300 mm TOSOH TSK-GEL, Type G3000PW, preceded by a 7.5×75 mm guard column of the same material, is thoroughly equilibrated with purified water. After injection of a peptide analyte, a linear gradient to 5 mM tetrabutylammonium hydrogen sulfate is applied over 30 minutes. FIG. 1 exemplifies such separation of a potassium monopersulfate peptide from its neurotoxin precursor.

Neuraminidases employed for the demonstration and quantitation of inhibitory capacities of various peptide preparations were of viral, bacterial, and mammalian origins. For demonstration purposes, viral neuraminidases were represented by the live, attenuated viruses available, respectively, from Intervet, Inc. and the Schering-Plough Animal Health Corp. (Canine Parainfluenza Virus), Merck and Company, Inc. (Mumps Virus) and Medimmune, Inc. (Influenza A Virus). The Sendai Virus, a paramyxovirus obtained from the American Type Culture Collection, was propagated in chick embryos and employed for demonstration of the antiviral properties of the peptides in vivo. The bacterial neuraminidase was a derivative of *Vibrio cholera* available from the Sigma Chemical Company. Mammalian neuraminidase was a component of a pool of dilute sputum fluids from patients with pulmonary tuberculosis.

A substrate for neuraminidase enzyme assays employed herein is 4-methyl-umbelliferyl-neuraminic acid obtained from commercial sources (i.e., Sigma Chemical Company). Enzyme reactions are carried out in 0.10 M chloride-free acetate buffers at pH 5.5, the optimum pH for the viral enzyme. Depending on the viral enzyme under analysis calcium ions, approximately 0.025 M, may be required. Enzyme reactions are terminated by additions of a stop buffer consisting of 0.2 M glycine buffer, pH 10.0, 25 percent with respect to ethanol. Fluorescence of the hydrolytic product, methylumbelliferone (MUF) is compared to that of standard aqueous solutions of the same fluorogen. Fluorescence measurements are at an excitation wavelength of 425 nm with emission detected at 539 nm. Quality controls for the analytic system involved simultaneous assays for the stable neuraminidase present in sputum fluids from patients with pulmonary tuberculosis. In a kinetic-analytic mode, the stop buffer is added to periodic aliquots withdrawn from mixtures of the enzyme source with substrate and buffer or inhibitor. Since these reactions are always linear (FIG. 2) measurements of the enzyme and inhibitors can also be determined at fixed reaction times in microtiter plates.

Figure 3:
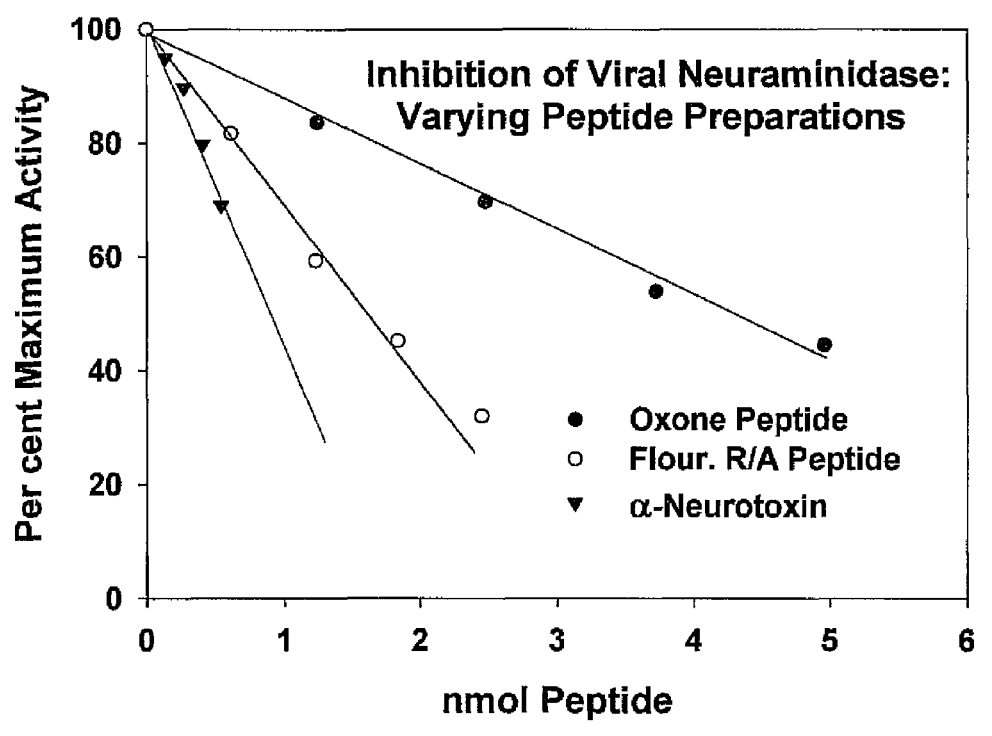

FIG. 3 illustrates (1) the neuraminidase inhibition phenomenon, and (2) the method for quantitative measurement of that inhibitory activity. In this case, the inhibitors are a potassium monopersulfate oxidized peptide, a reduced toxin alkylated with iodoacetamide, and the native toxin from which those peptides are derived. The enzyme source is the canine parainfluenza virus. The enzyme substrate is methyl-umbelliferyl-neuraminic acid (MUN). Periodically, aliquots from the enzyme-peptide interactions were treated with the alkaline stop buffer followed by measurements of the fluorescent product, methylumbelliferone. The retained neuraminidase inhibitory capacities of the toxin and its detoxified derivatives indicate presence of common, rigid, molecular sites unaffected by both the scission of the disulfide bonds and the conformational reorganizations that follow that event.

Figure 4:
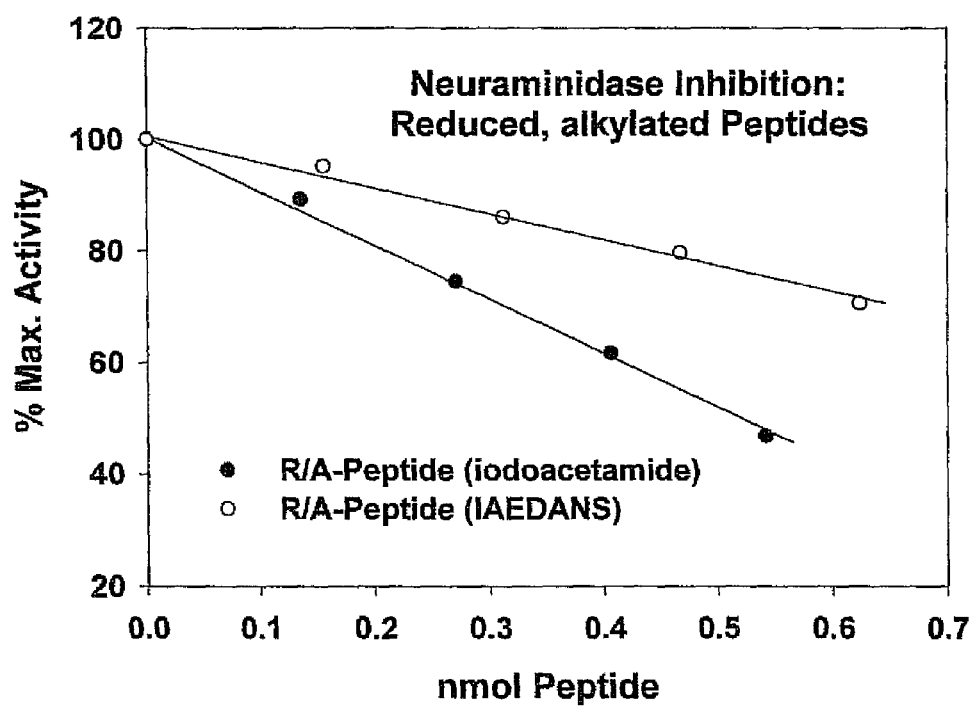
FIG. 4 is a graph that compares viral neuraminidase inhibition by different reduced and alkylated peptides. Thus, potency of the subset of neuraminidase inhibitors produced by reduction and alkylation of alpha-neurotoxins may vary with the alkylation adduct. The peptide, alkylated here with iodoacetamide, was reduced in dithiothreital. The peptide alkylated with 5-((((iodoacetyl)amino)ethyl)amino)naphthalene-1-sulfonic acid (IAEDANS) was reduced in Tris-(2-carboxyethyl) phosphene.

As described above, the active alpha-neurotoxin, the potassium monopersulfate oxidized peptide, and members of the reduced, alkylated subset inhibit the viral neuraminidase. Alkylating agents for the two members of the subset depicted in FIG. 4 are iodoacetamide and IAEDANS. The latter of the two subset members is fluorescent. Therefore, its antiviral activity and fluorescence provide an indicator for study of the antiviral effect. The data also indicate that antiviral potency of a peptide varies with the nature of the alkylation adduct.

The data of FIG. 5 confirm, by physical means, inhibition of the neuraminidase of the canine parainfluenza virus, in this case by a reduced, alkylated peptide. Toxin reduction was in Tris-(2-carboxyethyl) Phosphene with 5-((((iodoacetyl) amino) ethyl)amino) naphthalene-1-sulfonic acid (IAEDANS) as alkylation reagent. The test system utilized Sephadex G-50 chromatography columns that separate the reactants from one another. The chromatographs are operated in chloride-free acetate buffers, pH 5.5, the optimum pH for the viral neuraminidase action. The viral neuraminidase elutes with the void volume of those columns. The neuraminidase peak height is lowered in the presence of the fluorescent peptide. Small amounts of the fluorescent peptide also appear in the enzyme peak (FIG. 5). The latter phenomenon associates the enzyme inhibition with formation of a peptide-virus complex.

Figure 6:
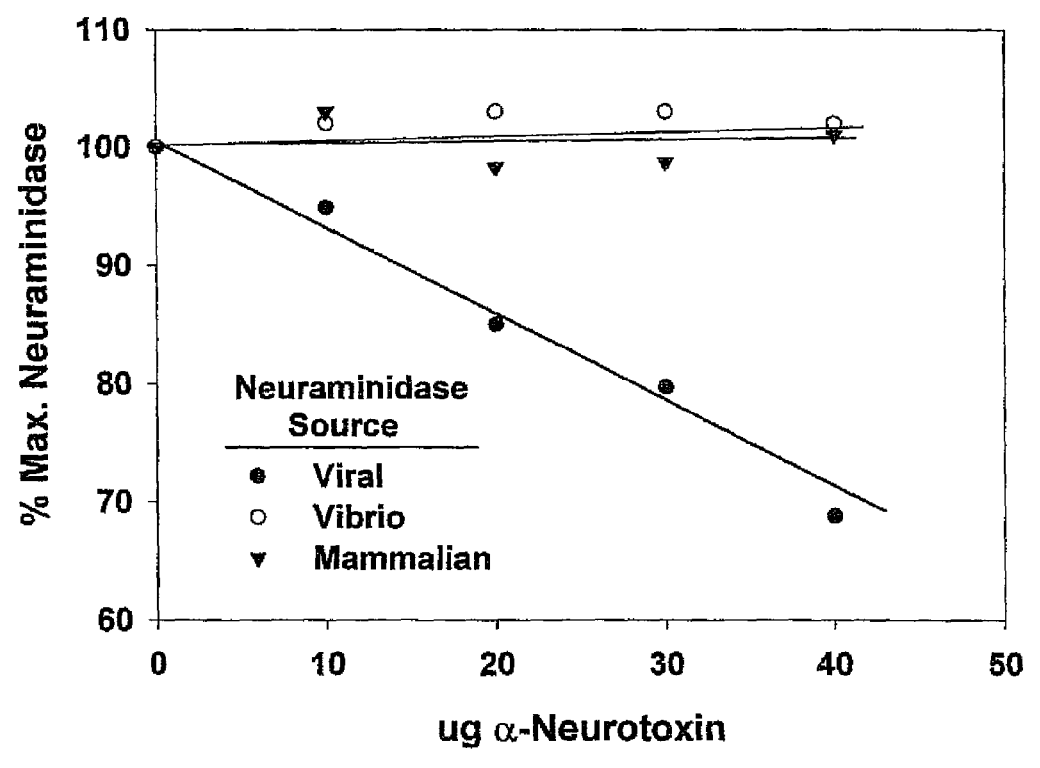

While the alpha-neurotoxin and the oxidized and reduced, alkylated peptides inhibit the viral neuraminidases, they do not inhibit bacterial and mammalian sources of that enzyme under the same test conditions. That phenomenon suggests specificity for the viral enzyme-peptide interactions. FIG. 6 represents that phenomenon employing the purified, unmodified alpha-neurotoxin as inhibitor.

Figure 7:
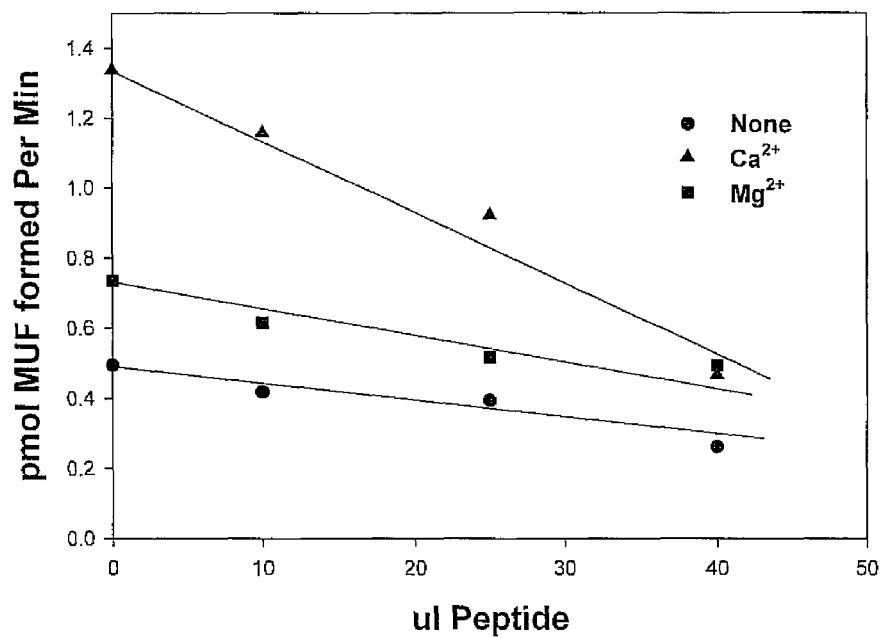
FIG. 7 is a graph displaying two phenomena concerning mumps virus neuraminidase and its inhibition by the peptides, in this case the potassium monopersulfate peptide. (1) The mumps neuraminidase is enhanced in the presence of calcium ions (0.025M). That phenomenon was reported as variable among strains of Influenza A virus (Baker, N. J. and Gandhi, S. S., Arch. Virol. (1976) 52, 7-18: Brett, B. C. and Johansson, I. C., J. Biochem. 134, 345-352 (2003)). (2) Equally important is the enhanced inhibition of the mumps virus neuraminidase by the peptide at the same calcium ion levels.

The data in FIG. 7 display two different phenomena concerning mumps virus neuraminidase and its inhibition by the peptides. First, the mumps neuraminidase is enhanced in the presence of calcium ions (0.025M). This phenomenon was reported as variable among strains of Influenza A virus (Baker, N. J. and Gandhi, S. S., Arch. Virol. (1976) 52, 7-18: Brett, B. C. and Johansson, I. C., J. Biochem. (2003) 134, 345-352). Equally important is inhibition of the mumps virus neuraminidase by the potassium monopersulfate oxidized peptide when enhanced at the same calcium ion levels.

Figure 8:
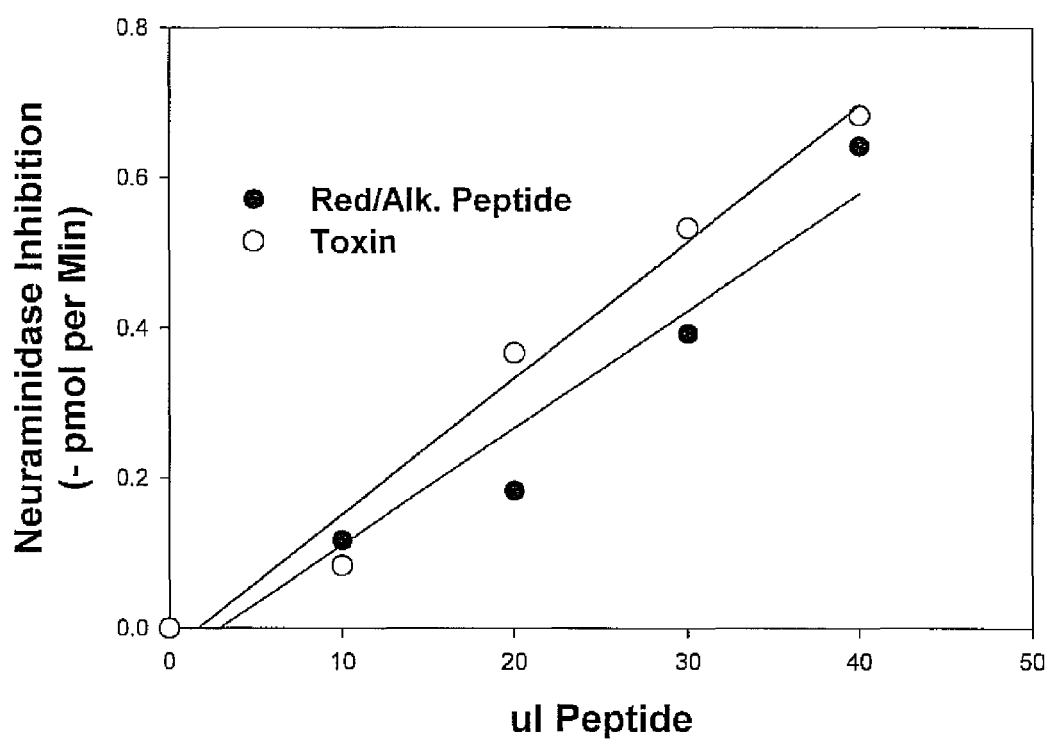
FIG. 8 is a graph displaying that the inhibition of mumps virus neuraminidase is also accomplished by the native toxin and a reduced, alkylated derivative. All such mumps virus neuraminidase inhibition reactions by the peptides require calcium ions.

Inhibition of mumps virus neuraminidase is also accomplished by varying forms of the antiviral peptide, in this case by the native toxin and by a reduced, alkylated derivative, as shown in FIG. 8.

Influenza A neuraminidase is also inhibited by the antiviral peptides, in this case by the parent neurotoxin, with calcium ions required for the phenomenon, as shown in FIG. 9. Inhibiting Influenza A neuraminidase is extremely critical in being able to treat and prevent "avian flu."

Tissue culture sheets of virus-permissive baby hamster kidney cells (BHK-21), available from the American Type Culture Collection, were infected with Semliki Forest Virus (SFV) produced in the same cells. In separate studies, the cells were treated with two preparations of reduced, alkylated peptides (A and B). Each was formed from 1.6 μmol purified alpha-neurotoxin in 1.0 mM EDTA and reduced in 4.8 mM dithiothreital at pH 7.5. Both were alkylated in 40 mM iodoacetamide, with pH adjustments to 7.0 with dilute ammonium hydroxide. The oxidized peptides were formed in 173 mM hydrogen peroxide and 0.60 mM copper sulfate as catalyst. All the peptides were evaluated for their abilities to reduce virus-induced plaque formation. Results (TABLE I) indicate equivalent antiviral potencies of the reduced, alkylated peptides and the oxidized peptides in protection of permissive BHK tissue culture cells against the neurotropic SFV.

Both the oxidized and reduced, alkylated forms of the antiviral peptides bind more than 98 percent of $Tc^{99}$ and $Tc^{99m}$ when mixed with $^{99}Tc$-pertechnetate and $^{99m}Tc$-pertechnetate in the presence of dilute stannous chloride and hydrochloric acid. Pharmacokinetic and biodistribution studies of the fate of the oxidized $^{99m}Tc$-peptide in humans and rabbits indicate the following:

1. Ninety-three percent of the peptide occurs free in plasma.
2. The peptide is excreted through the kidneys.
3. The peptide is degraded to smaller $^{99m}Tc$-peptide fragments on excretion into the bladder.
4. Quantitative plasma levels following intravenous and intramuscular injection are typical of, respectively, 2- and 3-compartment kinetic systems.
5. TABLE II includes mean pharmacokinetic parameters from intravenous injections in three human subjects.

6. Rate constant for absorption from the intramuscular site is 390 ug per hour, with steady-state onset in 13-14 hours.

Figure 10:
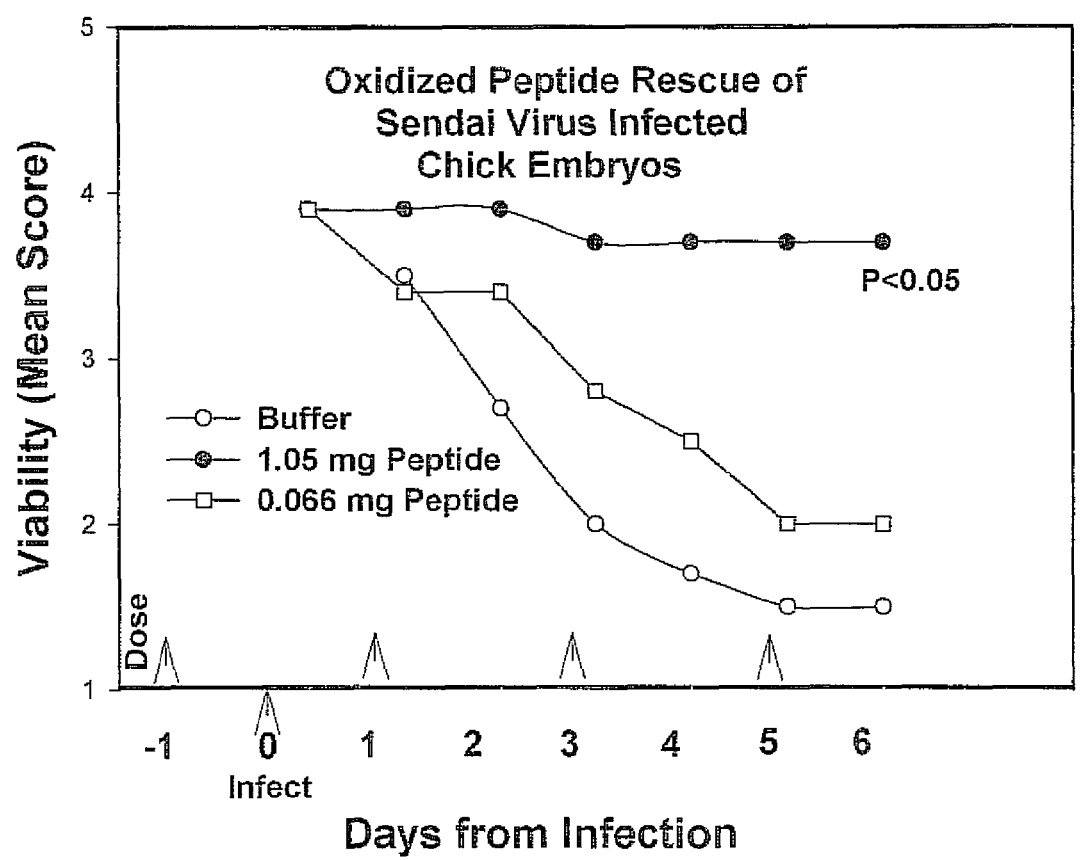
FIG. 10 is a graph displaying the protection of chick embryos from Sendai Virus infections. Groups of nine-day embryonated eggs received, respectively, phosphate buffered saline as placebo, and two quantities of an oxidized peptide preparation instilled in the allantoic sacs. On day 10 all eggs were infected with the Sendai Virus. On days 11, 13, and 15 the same quantities of placebo and peptide were again administered. Mean embryo viabilities are recorded from the day of infection. The surviving embryos hatched as normal chicks.

Animal studies were conducted to demonstrate the protective action of the oxidized form of the peptide in chicken embryos experimentally infected with the Sendai Virus (SV). SV is a neuraminidase-containing parainfluenza virus of the myxovirus family. Groups of nine-day old chick embryos were treated, respectively, with injections into the allantoic sacs of phosphate buffered saline as placebo and two levels of an oxidized antiviral peptide. The next day (day 10) all embryos were infected with the Sendai Virus. The day after infection (day 11), and every other day thereafter (days 13 and 15), treatments with the respective agents were resumed. Viabilities of the embryos were monitored daily to hatching time. Results are recorded in FIG. 10 with surviving embryos hatching as normal chicks. Thus, the chicks were protected by administration of the antiviral peptides.

This peptide-induced salvage of chick embryos from a myxovirus infection prompted application of the various products to therapeutic efforts in mammals. Systematic studies were initiated following favorable anecdotal results from applications of several forms of the peptides to small animal diseases identified above. Three groups of cats, symptomatically and serologically positive for feline leukemia (FeL) and/or feline immunodeficiency virus (FIV), were treated with subcutaneous injections of the peptides. Data in TABLE III summarize results of those studies. The animals in each group were those that completed therapies until the laboratory tests were completed. Other treated animals, not represented in the table, demonstrated clinical improvements but were withdrawn by the owners before laboratory tests could be completed. The clinical improvements were associated with consistent reversal of the immunofluorescence (IFA) test for FeL. The more sensitive ELIZA test for the same virus was reversed in most, but not all of the patients (TABLE III).

Unusual results were obtained from treatments of five dogs with malignant melanoma, those tumors in the oral region. Daily peptide injections over thirty days produced significant reduction in swelling and necrosis in the lesions. The tumors were then removed surgically, followed by further 30-day peptide treatments. No recurrences were evident.

The antiviral peptides of the present invention can be manufactured as therapeutic agents. They are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the antiviral peptides of the present invention can be administered in various ways. It should be noted that they can be administered as the compound and can be administered alone or as an active ingredient in combination with pharmaceutically acceptable carriers, diluents, adjuvants and vehicles. The compound can also be administered with other active ingredients. The peptides can be administered orally, subcutaneously or parenterally including intravenous, intraarterial, intramuscular, intraperitoneally, intratonsillar, and intranasal administration as well as by intrathecal and infusion techniques. Implants of the compounds are also useful. The compound can be administered by sustained- and controlled-release methods known in the art. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days, or over a longer period of time. The treatment generally has a length proportional to the length of the disease process and drug effectiveness and the patient species being treated.

When administering the compound of the present invention parenterally, it can generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233, 4,447,224; 4,439,196; and 4,475,196. Many other such implants, delivery systems, and modules are well known to those skilled in the art.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Antiviral Activities of Reduced/Alkylated and Oxidized Peptides

| Substance Tested | p.f.u.* | % Inhibition |
|---|---|---|
| Control | $10^{8.4}$ | — |
| Oxidized Prep. A | $10^{7.1}$ | 94.9 |
| Oxidized Prep. B | $10^{6.0}$ | 99.6 |
| Reduced/Alkylated Prep. A | $10^{6.0}$ | 99.6 |
| Reduced/Alkylated Prep. B | $10^{6.7}$ | 98.0 |

*Plaque forming units induced by 0.2 ml Semliki Forest Virus on BHK cells.

TABLE II

Pharmacokinetic Parameters of [$^{99m}$Tc] Neurotoxoid Administered Interavenously in Humans

| Parameters (Units) | Values (Range) |
|---|---|
| Biovailability (%)* | >90 |
| Steady State Onset (Hours) | 15-16 |
| $K_{el}$ (Hours$^{-1}$) | 0.0204 (0.0197-0.0214) |
| $T_{1/2}$ (Hours) | 33.9 (32.4-35.2) |
| $V_D$ (Liters/Kg)' | 0.262 (0.244-0.274) |
| $Cl_{ss}$ (Ml/Min/Kg) | 0.108 (0.102-0.115) |
| $V_{Dcl}$ (Liters/Kg)! | 0.319 (0.300-0.338) |

*Per cent unaltered plasma peptide in steady state

'Volume of distribution derived from plasma $K_{el}$

!Volume of distribution derived from $Cl_{ss}$

TABLE III

Three Groups of Cats: FeL-Positive and/or FIV-Positive
Therapy: Oxidized Peptide
Results: Effects on Immunologic Detection Tests

| # CATS | IFA-NEG. | ELIZA-NEG |
|---|---|---|
| 31 | 31 (100%) | 26 (83.9%) |
| 21 | 21 (100%) | 16 (76.2%) |
| 10 | 10 (100%) | — |

The invention claimed is:

1. A peptide-containing composition comprising an isolated peptide, wherein:

(a) the peptide comprises the amino acid sequence of a native α-neurotoxin;

(b) the cysteines normally involved in forming disulfide bonds are oxidized so they are unable to form disulfide bonds, such that none of the peptides in the composition have disulfide bonds;

(c) the amino acids of the peptide are unmodified, except for lacking disulfide bonds; and, (d) the peptide has antiviral activity.

2. The composition of claim 1, wherein the native α-neurotoxin is a Type I α-neurotoxin.

3. The composition of claim 1, wherein the native α-neurotoxin is a Type II α-neurotoxin.

4. The composition of claim 1, wherein the native α-neurotoxin is selected from the group consisting of venom α-neurotoxins.

5. The composition of claim 1, wherein the native α-neurotoxin is from a snake selected from the group consisting of a cobra, a banded krait and *Crotalus duressus terrificus*.

6. The composition of claim 1, wherein the composition is capable of preventing or treating infection by at least one virus.

7. The composition of claim 6, wherein the virus belongs to a family selected from the group consisting of Orthomyxoviridae and Paramyxoviridae.

8. The composition of claim 6, wherein the virus is selected from the group consisting of Semliki Forest Virus, Influenza A virus, Influenza B virus, Influenza C virus, Mumps virus, Sendai virus, Newcastle Disease virus, Canine distemper virus, adenovirus type 2, coronavirus, Parainfluenza virus, Canine parvovirus, Feline parvovirus, herpesvirus, Feline calicivirus, Feline leukemia virus, and Feline immunodeficiency virus.

9. The composition of claim 1, wherein the composition is capable of preventing or treating infection by viruses in a family selected from the group consisting of Orthomyxoviridae, and Paramyxoviridae.

10. The composition of claim 1, wherein the composition inhibits viral neuraminidase enzyme activity.

11. The composition of claim 10, wherein the virus belongs to a family selected from the group consisting of Orthomyxoviridae and Paramyxoviridae.

12. The composition of claim 10, wherein the virus is selected from the group consisting of influenza virus, Mumps virus, Sendai virus, Newcastle Disease virus, canine distemper virus and parainfluenza virus.

13. A method for treating and/or inhibiting viral infection in a patient in need of such treatment or inhibition, the method comprising administering a composition to the patient, wherein the composition comprises an isolated peptide, wherein:

(a) the peptide comprises the amino acid sequence of a native α-neurotoxin;

(b) the cysteines normally involved in forming disulfide bonds are oxidized so they are unable to form disulfide bonds, such that none of the peptides in the composition have disulfide bonds;

(c) the amino acids of the peptide are unmodified, except for lacking disulfide bonds; and, (d) the peptide has antiviral activity.

14. The method of claim 13, wherein the patient is infected with a virus.

15. The method of claim 13, wherein the patient is not infected with a virus.

16. The method of claim 13, wherein the α-neurotoxin is a Type I α-neurotoxin.

17. The method of claim 13, wherein the α-neurotoxin is a Type II α-neurotoxin.

18. The method of claim 13, wherein the α-neurotoxin is selected from the group consisting of venom α-neurotoxins.

19. The method of claim 13, wherein the α-neurotoxin is from a snake selected from the group consisting of a cobra, a banded krait and *Crotalus duressus terrificus*.

20. The method of claim 13, wherein the virus belongs to a family selected from the group consisting of Orthomyxoviridae and Paramyxoviridae.

21. The method of claim 13, wherein the virus is selected from the group consisting of Semliki Forest Virus, Influenza A virus, Influenza B virus, Influenza C virus, Mumps virus, Sendai virus, Newcastle Disease virus, Canine distemper virus, adenovirus type 2, coronavirus, Parainfluenza virus, Canine parvovirus, Feline parvovirus, herpesvirus, Feline calicivirus, Feline leukemia virus, and feline immunodeficiency virus.

22. The method of claim 13, wherein the composition inhibits viral neuraminidase enzyme activity.

23. The method of claim 22, wherein the virus belongs to a family selected from the group consisting of Orthomyxovirida and Paramyxoviridae.

24. The method of claim 22, wherein the virus is selected from the group consisting of Influenza A virus, Influenza B virus, Influenza C virus, Mumps virus, Sendai virus, Newcastle Disease virus, Canine distemper virus, Parainfluenza virus, Canine parvovirus, Feline parvovirus, herpesvirus, Feline calicivirus, Feline leukemia virus, and Feline immunodeficiency virus.

* * * * *